United States Patent [19]

Isogai et al.

[11] Patent Number: 5,689,325
[45] Date of Patent: Nov. 18, 1997

[54] OPHTHALMOLOGIC APPARATUS WITH EASE OF OPERATION

[75] Inventors: Naoki Isogai; Masamichi Suzuki, both of Aichi, Japan

[73] Assignee: Nidek Co., Ltd., Gamogori, Japan

[21] Appl. No.: 634,616

[22] Filed: Apr. 19, 1996

[30] Foreign Application Priority Data

Apr. 19, 1995 [JP] Japan ............................ 7-119220
Apr. 19, 1995 [JP] Japan ............................ 7-119221

[51] Int. Cl.$^6$ ........................... A61B 3/14; A61B 3/00
[52] U.S. Cl. ................................. 351/208; 351/245
[58] Field of Search .......................... 351/205, 208, 351/245

[56] References Cited

U.S. PATENT DOCUMENTS

| | | | |
|---|---|---|---|
| 5,212,507 | 5/1993 | Fujieda et al. | 351/212 |
| 5,406,076 | 4/1995 | Mimura et al. | 250/229 |
| 5,589,899 | 12/1996 | Maeda et al. | 351/208 |

FOREIGN PATENT DOCUMENTS

646999 2/1994 Japan .
6285025 10/1994 Japan .

*Primary Examiner*—Huy Mai
*Attorney, Agent, or Firm*—Sughrue, Mion, Zinn, Macpeak & Seas, PLLC

[57] ABSTRACT

A measuring unit is mounted on a movable stage, which is movable in the right-left and front-rear directions relative to a fixed base stage. When an examiner moves the movable stage to the right or to the left by manipulating a joy stick, a micro switch detects that movement. Upon reception of a detection signal from the micro switch, a microcomputer allows power to be supplied to measurement circuits, to initiate a measurement mode. When judging that proper alignment has been established, the microcomputer automatically calculates a cornea shape. Measurement and calculation of a cornea shape are repeated until a standard deviation of measurement data falls within a given value. Upon completion of the measurement operation, the microcomputer stops the supply of power to the measurement circuits, to cancel the measurement mode.

8 Claims, 7 Drawing Sheets

OPHTHALMOLOGIC APPARATUS WITH EASE OF OPERATION

BACKGROUND OF THE INVENTION

1. Field of the Invention

The present invention relates to an ophthalmologic apparatus to be used for examination of eyes.

2. Description of the Related Art

Among known ophthalmologic apparatuses for examination of eyes are an eye's refracting power measuring apparatus, a cornea shape measuring apparatus, and a non-contact tonometer. In general, these ophthalmologic apparatuses have a joy stick mechanism that allows an examiner to move, with respect to a base stage, a movable stage on which a measuring unit is mounted by manipulating a operation lever called "joy stick." An alignment operation is performed by using the joy stick mechanism.

Figure 6:
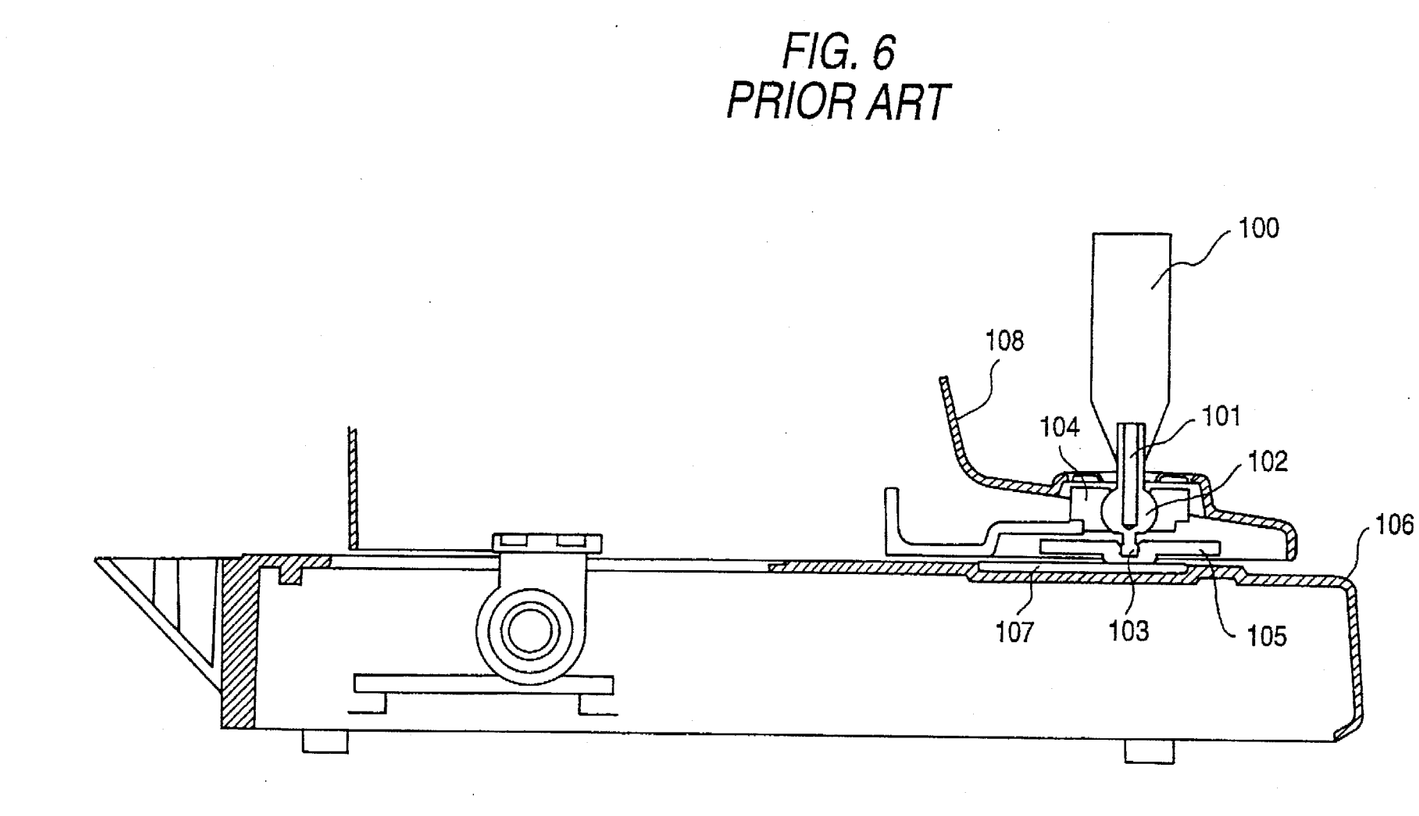
FIG. 6 illustrates a conventional joy stick mechanism.

FIG. 6 shows the structure of a known joy stick mechanism. A spherical portion 102 and a lower end portion 103 are provided below a shaft 101 that is inserted in an operation lever 100. The spherical portion 102 is held by a ball bearing 104, and the operation lever 100 is rotatable with the center of the spherical portion 102 serving as a fulcrum. As the operation lever 100 rotates, the lower end portion 103 swings a slide plate 105. Since a friction plate 107 that is bonded to the base stage 106 is in contact with the slide plate 105, fine horizontal movement of a movable stage 108 having a measuring unit is effected as the slide plate 105 swings on the friction plate 107.

The joy stick mechanism further has a stopper mechanism for fixing the movable stage when the entire apparatus is moved. The stopper mechanism includes a rubber stopper with screws.

After an alignment operation is finished, one eye is measured by manipulating operation switches. Thereafter, the other eye is measured. After completion of the measurements of both eyes, measurement data are output upon manipulation of a switch and the examiner turns off the power.

The above conventional apparatus has advantages that correct alignment can be attained and that an examiner can perform measurements while confirming those one by one.

On the other hand, the above conventional apparatus is disadvantageous in that a switch operation is needed for each step of a measurement procedure, which is cumbersome. The value of measurement data depends on the skill of an examiner. Further, an examination takes relatively long time.

Moreover, the joy stick mechanism is costly, because it is complex in structure and hence has many parts.

SUMMARY OF THE INVENTION

In view of the above-described problems of the conventional apparatus, an object of the present invention is to provide an ophthalmologic apparatus that requires a smaller number of switch operations and is therefore easy to operate.

Another object of the invention is to provide an ophthalmologic apparatus that is simple in structure and therefore enables an easy alignment operation.

To attain the above objects, according to a first aspect of the invention, there is provided an ophthalmologic apparatus comprising measuring means for measuring an eye of a subject; a movable stage on which the measuring means is mounted; moving means for moving the movable stage horizontally relative to a fixed base stage; recognizing means for recognizing whether the measuring means has been moved by the moving means so as to go out of a predetermined range; and transition means for starting supply of power to the measuring means based on a recognition result of the recognizing means, to thereby render the measuring means operational.

According to a second aspect of the invention, there is provided an ophthalmologic apparatus comprising measuring means for measuring an eye of a subject; a movable stage on which the measuring means is mounted; moving means having an operation lever incapable of inclination, for moving the movable stage horizontally relative to a fixed base stage; recognizing means for recognizing whether the measuring means has been moved by the moving means so as to go out of a predetermined range; transition means for starting supply of power to the measuring means based on a recognition result of the recognizing means, to thereby render the measuring means operational; an alignment detection optical system for projecting alignment targets to the eye and for detecting the projected alignment targets; judging means for judging an alignment state based on a detection result of the alignment detection optical system; and measurement instructing means for instructing, based on a judgment result of the judging means, the measuring means to start measuring the eye.

According to a third aspect of the invention, there is provided an ophthalmologic apparatus comprising measuring means for measuring an eye of a subject; a movable stage on which the measuring means is mounted; moving means for moving the movable stage horizontally relative to a fixed base stage; first recognizing means for recognizing whether the measuring means has been moved by the moving means so as to go out of a predetermined range; transition means for starting supply of power to the measuring means based on a recognition result of the first recognizing means, to thereby render the measuring means operational; second recognizing means for recognizing whether the measuring means has completed output of measurement data; stopping means for stopping the supply of the power to the measuring means based on a recognition result of the second recognizing means.

DESCRIPTION OF THE PREFERRED EMBODIMENT

An embodiment of the invention will be hereinafter described with reference to the accompanying drawings.

Entire Configuration

Figure 1:
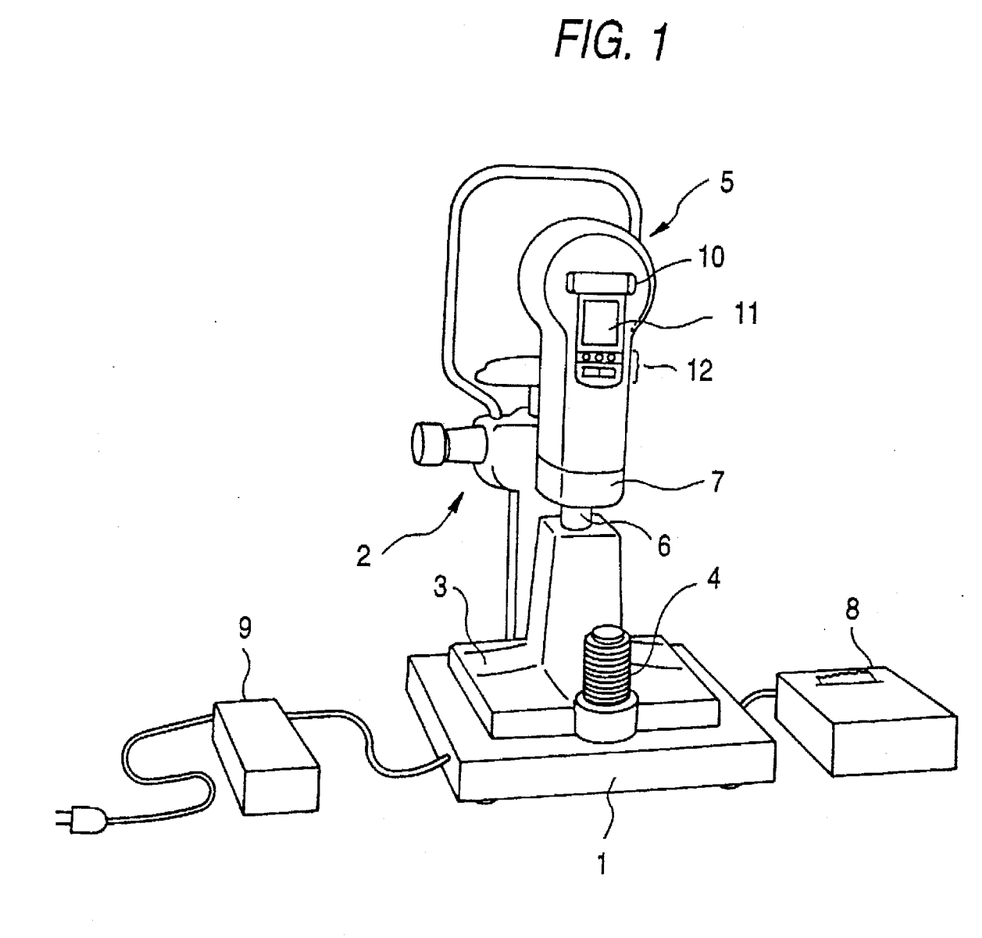
FIG. 1 shows a general appearance of a cornea shape measuring apparatus according to an embodiment of the present invention.

FIG. 1 shows a general appearance of a cornea shape measuring apparatus according to the embodiment. Reference numeral 1 denotes a base stage. A head support portion 2, on which the head of a subject is to rest, is fixed to the base stage 1. Reference numeral 3 denotes a movable stage that moves on the base stage 1 in accordance with manipulation of a joy stick 4.

Reference numeral 5 denotes a measuring unit that accommodates an optical system for observation and an electrical system for control and computation. Mounted on a vertical movement shaft 6 that is held by the movable stage 3 so as to be movable vertically, the measuring unit 5 is moved vertically by rotating a rotary knob 4a of the joy stick 4. The measuring unit 5 of this embodiment is detachable from a connection member 7 that is fixed to the vertical movement shaft 6. Therefore, by removing the measuring unit 5 from the connection member 7 and connecting a battery (not shown) to it, it can be used as a hand-held cornea shape measuring apparatus.

The measuring unit 5 has an observation window 10, a liquid crystal display 11 for displaying a measurement result and other information, and operation switches 12 such as a print switch and a parameter setting switch.

Reference numeral 8 denotes a printer for printing out measurement data produced by the measuring unit 5, and numeral 9 denotes an AC adaptor for supplying power to the apparatus.

Configurations of Respective Components

Configurations of the main components of the apparatus of this embodiment will be described below.

Optical System

Figure 2:
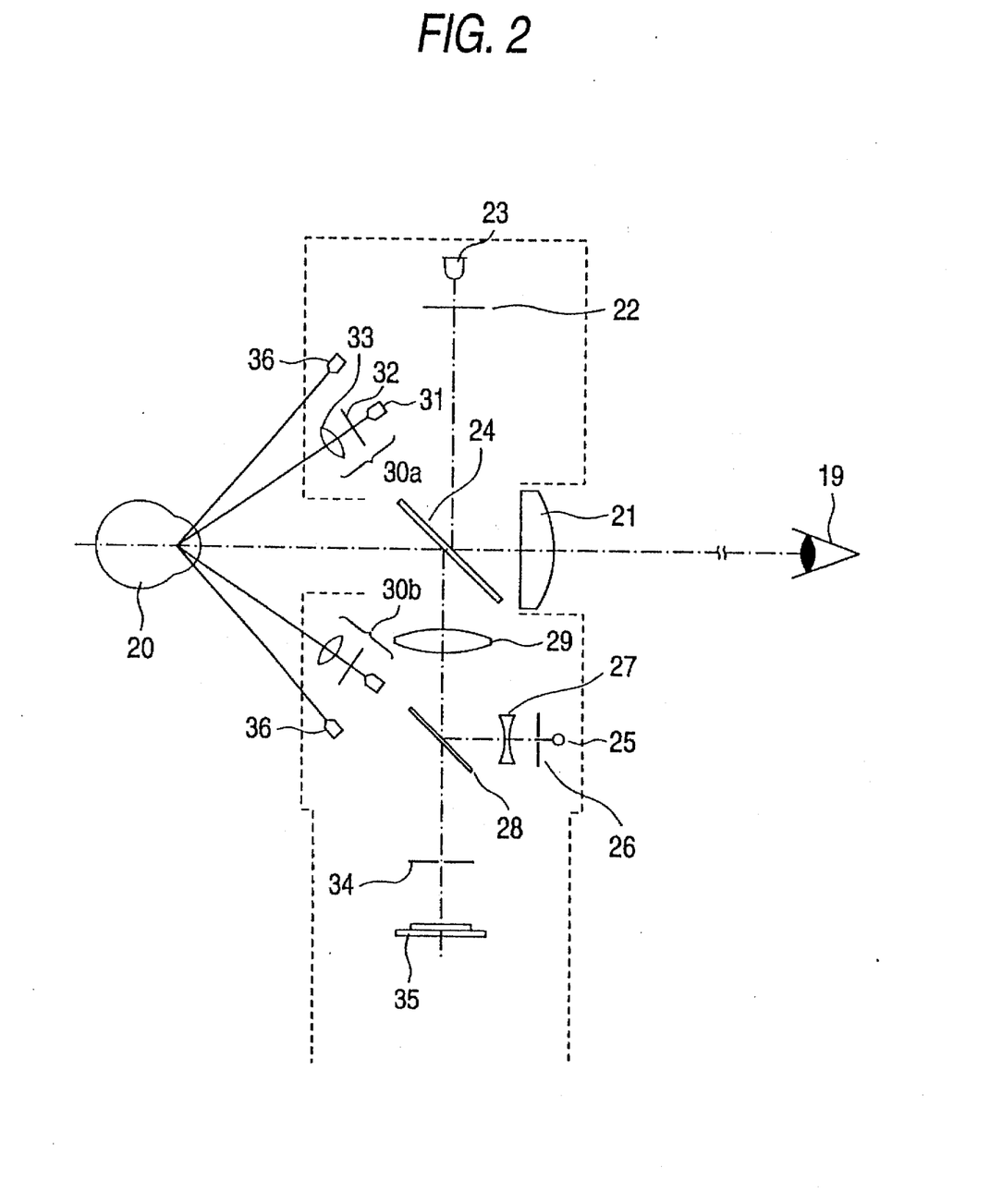
FIG. 2 schematically shows the arrangement of an optical system provided in a measuring unit.

FIG. 2 schematically shows the arrangement of an optical system provided in the measuring unit 5. An examiner's eye 19 observes an enlarged image of a subject's eye 20 via an objective lens 21. Reference numerals 22 and 23 denote an alignment mark plate and an illumination light source, respectively. When the illumination light source 23 is turned on, a light beam emitted therefrom passes through the alignment mark plate 22 to become a light beam representing the alignment mark, which is then reflected by a beam splitter 24 and thereby directed to the examiner's eye 19. The examiner performs an alignment operation while observing an enlarged image of the front portion of the subject's eye 20 through the observation window 10 with the alignment mark superimposed on the image of the subject's eye 20.

Reference numerals 25–27 denote a fixation target light source, a fixation target plate having a spot opening, and a concave lens, respectively. Reference numeral 28 denotes a dichroic mirror that makes the optical axis of a target detection optical system (described later) and the projection optical system of the fixation target coincide with each other, and numeral 29 denotes an imaging lens. Illuminated with light emitted from the light source 25, the fixation target plate 26 is projected onto the fundus of the subject's eye 20 via the dichroic mirror 28 and the beam splitter 24 by means of the concave lens 27 and the imaging lens 29. Thus, the subject's eye 20 can stare at the fixation target plate 26.

A target projection optical system 30 is made up of eight optical systems that are arranged on a circle around the observation optical axis at intervals of 45°. The respective projection axes of the eight optical systems form given angles with the observation axis. Among the eight optical systems are four cornea shape measuring optical systems 30a–30d (optical systems 30c and 30d are not shown), each of which is composed of a light source 31 such as a near infrared LED, a spot stop 32, and a collimator lens 33 to cause the spot stop 32 to be regarded as if it were located at a point of infinity. The cornea shape measuring optical systems 30a–30d are also used as part of an optical system for working distance detection. That is, the optical system for working distance detection is constituted of the optical systems 30a–30d for projecting infinity light beams and optical systems 30e–30h (not shown; each being composed of a light source 31 and a spot stop 32) for projecting non-infinity light beams.

The target detection optical system is composed of the beam splitter 24, the imaging lens 29, a telecentric stop 34, and a two-dimensional position-sensitive device 35. The telecentric stop 34 is located at the focal point of the imaging lens 29. Located at a position that is conjugate, with respect to the imaging lens 29, with an iris and its vicinity where a cornea reflection image produced by the target projection optical system 30 is to be formed, the two-dimensional position-sensitive device 35 detects the cornea reflection image.

LEDs 36 are disposed on a circle around the observation optical axis at intervals of 30°, and cornea reflection images of the LEDs 36 serve, as a whole, as a mire ring. The LEDs 36 also serve to illuminate the front portion of the subject's eye 20.

Joy Stick Mechanism

Figure 3:
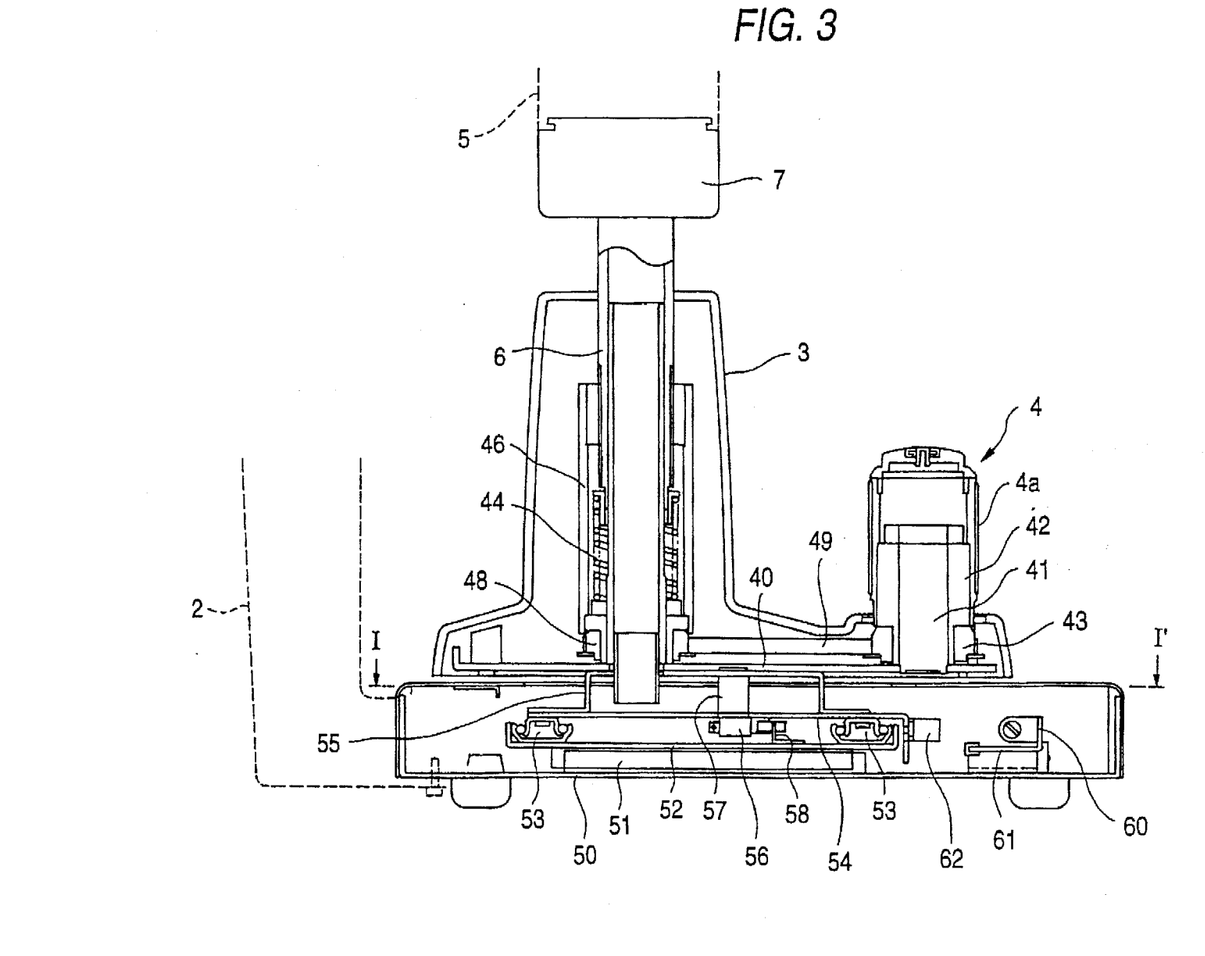
FIG. 3 is a sectional view showing a moving mechanism including a joy stick.
Figure 4:
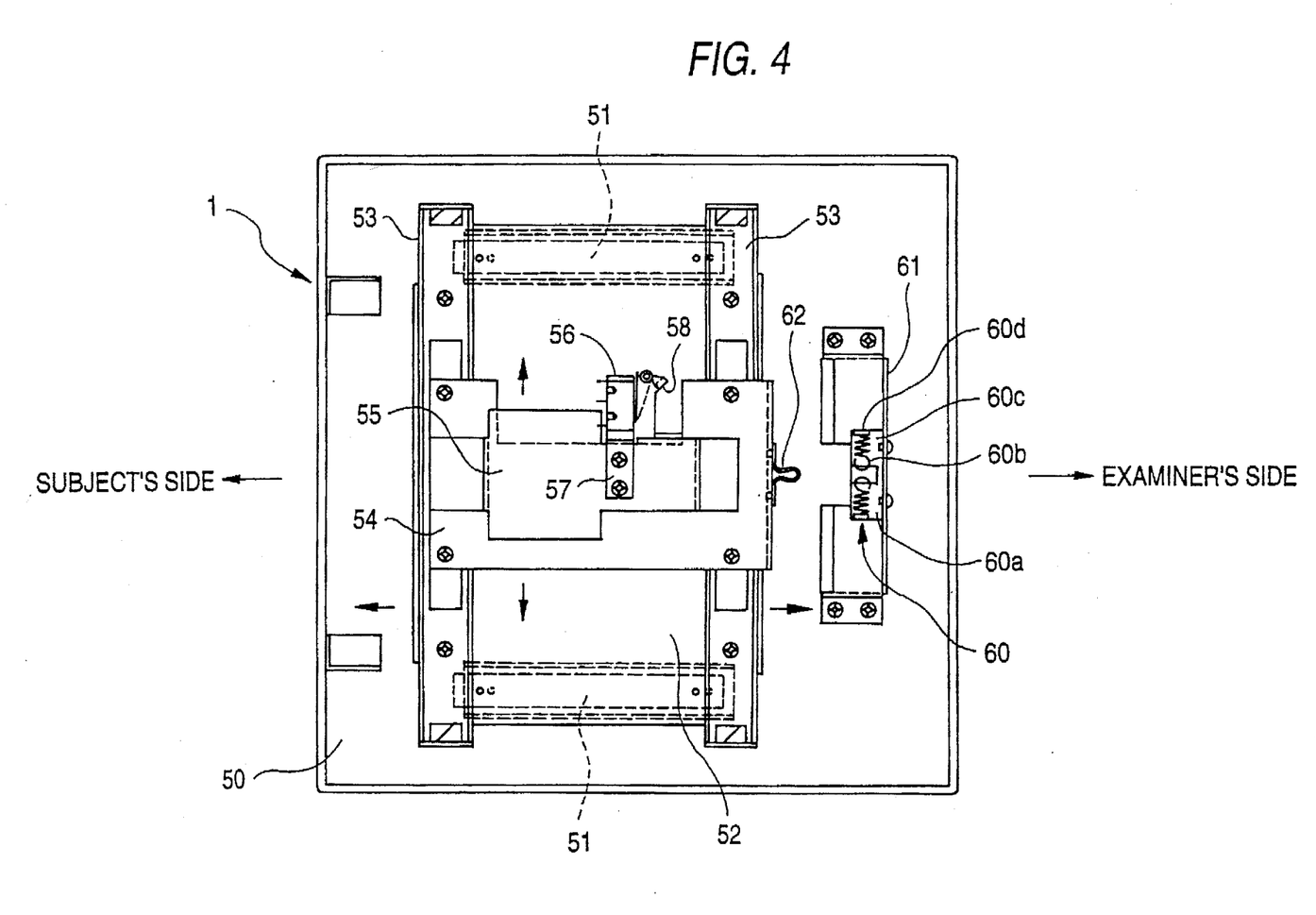
FIG. 4 is a top view as viewed when the portions above plane I–I' in FIG. 3 are taken away.

FIG. 3 is a sectional view showing a moving mechanism that includes a joy stick, and FIG. 4 is a top view as viewed when the portions above plane I–I' (see FIG. 3) are taken away. As for the moving mechanism, separate descriptions will be made of vertical and horizontal moving mechanisms.

The vertical moving mechanism is made up of a joy stick support rod 41 that is erected on a plate 40 of the movable stage 3, a bearing 42 that is rotatable about the joy stick support rod 41, a rotary knob 4a that is fixed to a top portion of the bearing 42, a gear 43 that is fixed to a bottom portion of the bearing 42, a measuring-unit-side support rod 44 that is erected on the plate 40, a cylinder 46 that is rotatable about the support rod 44 and is equipped with a feed nut, a vertical movement shaft 6 having a feed screw that is threadedly engaged with the feed nut of the cylinder 46, a gear 48 that is fixed to a bottom portion of the cylinder 46, and a belt 49 that is engaged with the gears 43 and 48. When the rotary knob 4a is rotated, the rotational force is transmitted to the cylinder 46 via the gear 43, the belt 49, and the gear 48. The rotation of the cylinder 46 causes vertical movement of the vertical movement shaft 6, thereby vertically moving the measuring unit 5.

The horizontal moving mechanism is made up of a lower substrate 52 that is supported by a base 50 of the base stage 1 through a pair of slide rails 51 so as to be movable in the front-rear direction (with respect to the examiner), an upper substrate 54 that is supported by the lower substrate 52 through a pair of slide rails so as to be movable in the right-left direction, and a support 55 for connecting the upper substrate 54 and the plate 40 of the movable stage 3. This configuration allows the movable stage 3 to move relative to the base stage 1 independently in the front-rear and right-left directions. The examiner can horizontally move the measuring unit 5 that is mounted on the movable stage 3 by manipulating the joy stick 4.

Right/Left Eyes Recognition Mechanism

Referring to FIGS. 3 and 4, reference numeral 56 denotes a micro switch that is attached to the plate 40 by means of a fixing plate 57, and numeral 58 denotes a guide plate that is attached to the lower substrate 52. As the plate 40 that is fixed to the movable stage 3 is moved in the right-left direction, the micro switch 56 also moves in the right-left direction (top-bottom direction in FIG. 4) relative to the lower substrate 52. As shown in FIG. 4, when the micro switch 56 is moved so as to be located to the left (lower side in FIG. 4) of approximately the center in the right-left direction, its contact comes to contact with the guide plate 58 to effect energization. Since the center in the right-left direction of the head of a subject which rests on the head support portion 2 approximately coincides with the center of the base stage 1 in the same direction, whether the right or left eye is going to be measured is recognized based on an on/off signal produced from the micro switch 56 that moves in the right-left direction.

Stopper Mechanism

Referring to FIGS. 3 and 4, reference numeral 60 denotes a ball catch that is fixed to the base 50 of the base stage 1 through a fixing plate 61, and numeral 62 denotes a protrusion member that is fixed to the upper substrate 54. The ball catch 60 is composed of two rigid balls 60b that are held by a recess member 60a, springs 60c that urge the respective rigid balls 60b toward the recess member 60a, and adjusting screws 60d for adjusting the urging force of the respective springs 60c.

The stopper mechanism is used when it is needed to fix the movable stage 3 to the base stage 1, for instance, when the apparatus is carried to another location. To effect fixing, after the movable stage 3 is positioned so that its center approximately coincides with the center of the base stage 1 in the right-left direction by manipulating the joy stick 4, the protrusion member 62 of the stopper mechanism is fitted into the ball catch 60 by pulling the joy stick 4 toward the examiner's side. To cancel the fixing of the movable stage 3, the joy stick 4 is pushed toward the subject's side. As a result, the protrusion member 62 is removed from the ball catch 60, so that the movable stage 3 becomes horizontally movable.

The protrusion member 62 and the ball catch 60 may be products on the market, in which case the manufacturing cost of the apparatus can be reduced.

Electrical System

Figure 5:
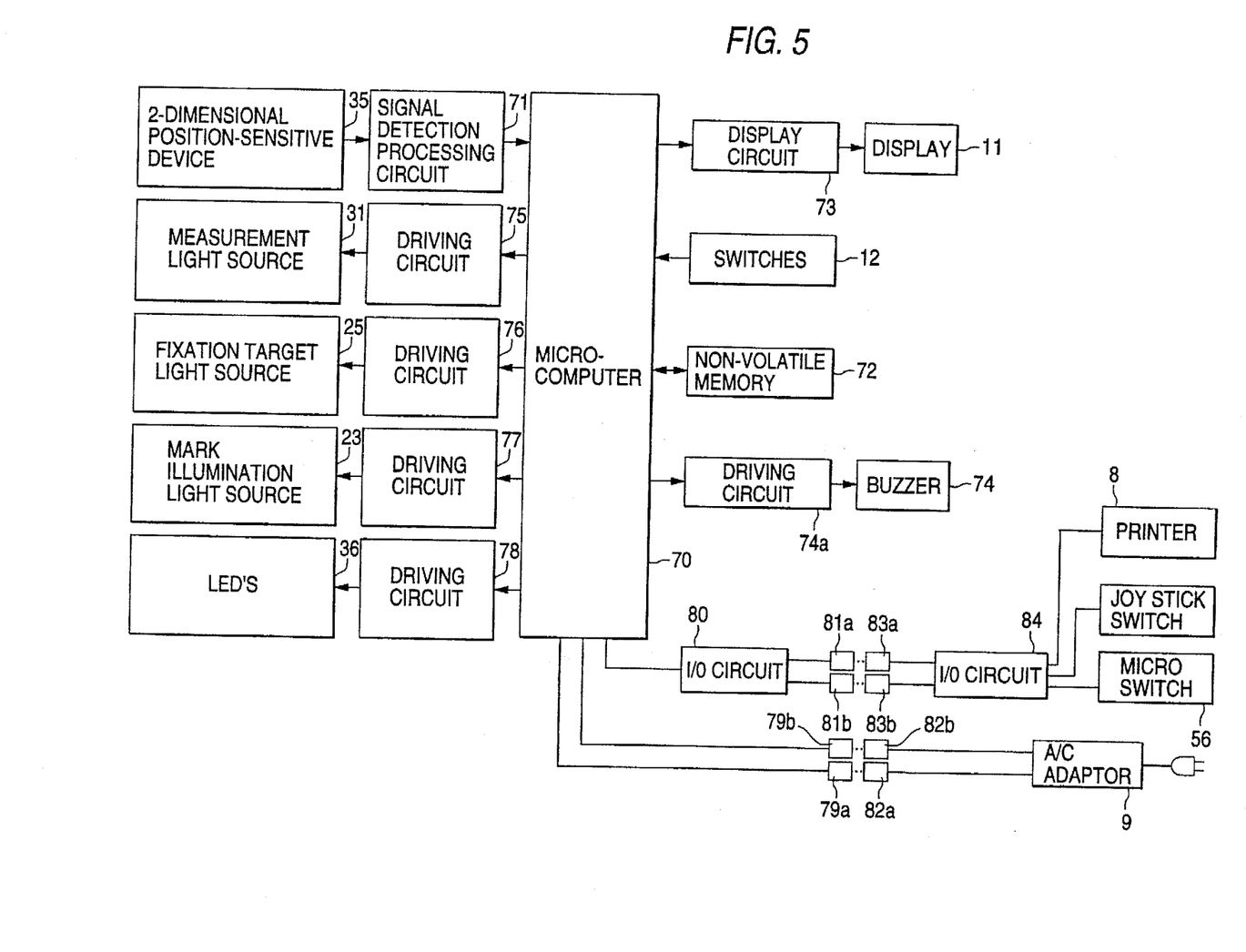
FIG. 5 is a block diagram showing the main part of an electrical system of the apparatus.

FIG. 5 is a block diagram showing the main part of the electrical system of the apparatus. A microcomputer 70 is incorporated in the measuring unit 5. The microcomputer 70 not only controls the entire apparatus, but also judges appropriateness of alignment and calculates a cornea shape by performing a given computing operation based on a detection signal originally produced by the two-dimensional position-sensitive device 35 and supplied via a signal detection processing circuit 71 that processes the detection signal in a predetermined manner.

Connected to the microcomputer 70 are a nonvolatile memory 72 for storing constants specific to the associated apparatus and other parameters, a display circuit 73 for the display 11, a driving circuit 74a for a buzzer 74, driving circuits 75–78 for driving the respective light sources, power contacts 79a and 79b for receiving power from the AC adaptor 9, and signal communication contacts 81a and 81b (via an input/output circuit 80). Contacts 82a and 82b, which are provided in the connection member 7 so as to correspond to the respective power contacts 79a and 79b, are connected to the AC adaptor 9. Contacts 83a nd 83b, which are also provided in the connection member 7 so as to correspond to the respective signal communication contacts 81a and 81b, are connected to an input/output circuit 84 to thereby allow signal communication with the micro switch 56 and the printer 8.

Figure 7:
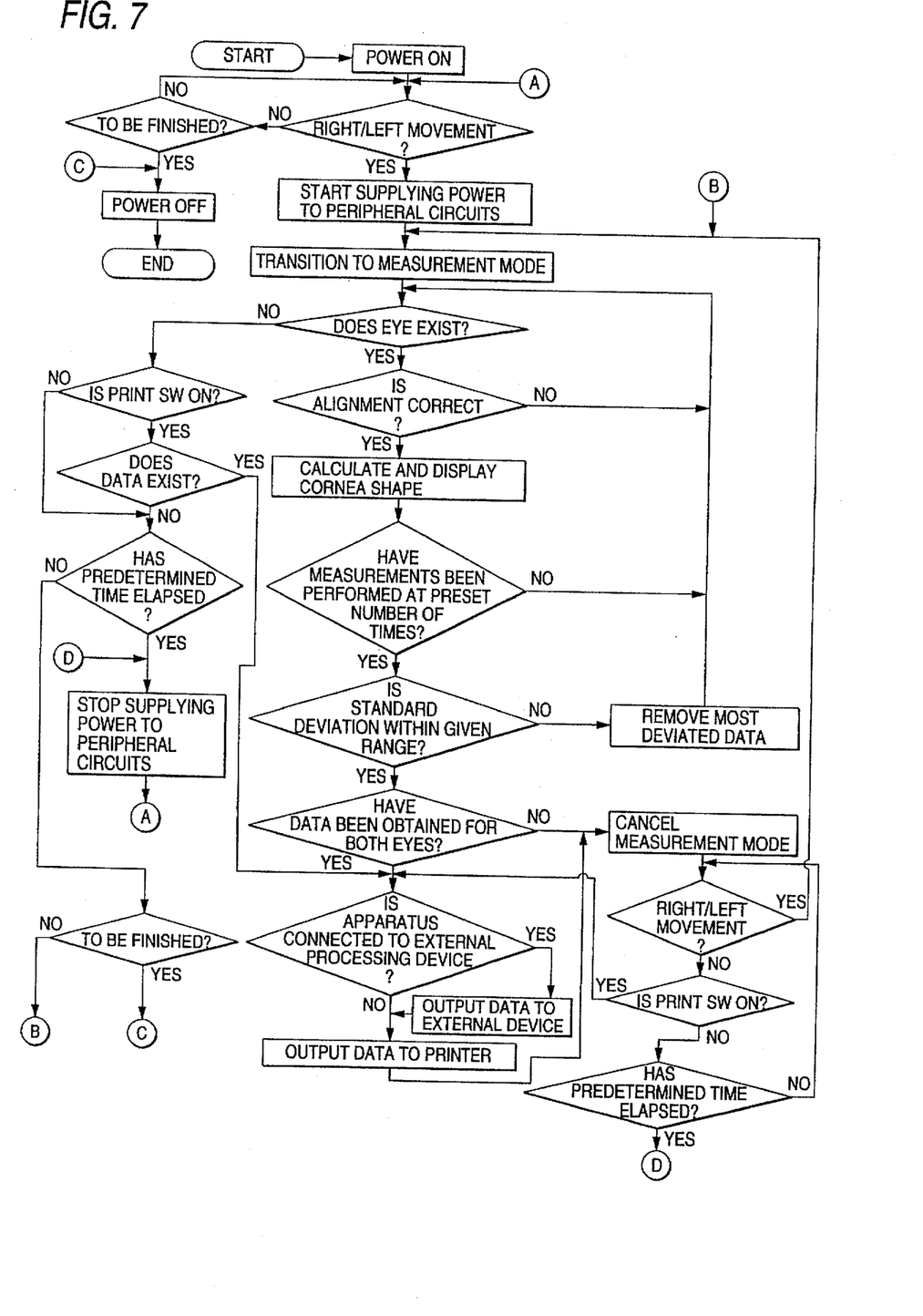
FIG. 7 is a flowchart showing the operation of the apparatus.

The operation of the apparatus having the above configuration will be hereinafter described (see FIG. 7).

When a power switch (not shown) that is provided in the AC adaptor 9 is turned on, power is supplied to the microcomputer 70 via the power contacts 82 and 79. At this stage, power is not supplied to the other electrical circuits and therefore a measuring operation is not performed. When the joy stick 4 is manipulated so as to move in the right-left direction, the micro switch 56 detects right/left switching and a resulting detection signal is input to the microcomputer 70. Upon reception of this signal, the microcomputer 70 drives the display 11 via the display circuit 73, and allows the other measurement circuits to receive power, to thereby render the apparatus ready for a measuring operation (this state is hereinafter called "measurement mode").

In the measurement mode, an examiner performs an alignment operation while observing the front portion of a subject's eye through the observation window 10 of the measuring unit 5. More specifically, the examiner moves the measuring unit 5 in the right-left direction together with the movable stage 3 by manipulating the joy stick 4 and moves the measuring unit vertically by rotating the rotary knob 4a so that the alignment mark has a prescribed relationship with an image of the front portion of the eye.

Then, the microcomputer 70 judges appropriateness of the alignment that has been attained by the moving operations of the examiner. Appropriateness of the alignment in the vertical and right-left directions is judged by obtaining differences between the centers of two opposed cornea reflection images and the measurement optical axis. Appropriateness of the alignment in the front-rear direction is judged by comparing heights of cornea reflection images that are formed by the infinity target projection optical systems 30a–30d and the non-infinity target projection optical systems 30e–30h. This is based on the fact that when the working distance is changed, the height of a cornea projection image produced by an non-infinity light source varies while that produced by an infinity light source does not. For details of the principle of this measurement, refer to U.S. patent application Ser. No. 08/098,786 (corresponding to Japanese Unexamined Patent Publication Nos. Hei. 6-46999 and Hei. 6-285025). When light source share the same projection optical axis, appropriateness of a working distance can be judged if one target image is obtained for each light source. In this embodiment, the microcomputer 70 determines an ellipse that connects cornea reflection images of the infinity target projection optical systems 30a–30d and an ellipse that connects cornea reflection images of the non-infinity target projection optical systems 30e–30h, extracting positions on a given meridian (for example, in a predetermined angular direction or in the direction of an astigmatism axis) of each ellipse, and compares the heights of those positions.

If the heights of the two kinds of images are within a given allowable range and if distances between the measurement optical axis and the centers of the cornea reflection images are within a given allowable range, the microcomputer 70 calculates a cornea shape based on the positions of the cornea reflection images produced by the target projection optical systems 30a–30d when the heights of the two kinds of images are judged within the given allowable range. As described in U.S. Pat. No. 5,212,507, if at least three target images are detected, a cornea shape can be calculated based on an ellipse that connects the three points. A measurement result is displayed on the display 11.

As described above, the apparatus judges appropriateness of alignment, and automatically calculates a measurement result if the alignment is judged within an allowable range. Therefore, even if the movement of the measuring unit 5 relative to the base stage 1 which movement is effected by the joy stick mechanism is rough, measurement can be performed in a correct alignment state.

The measurement and calculation of a cornea shape of one eye are performed at preset times continuously (the number of measurements for one eye can be set and changed by a parameter setting switch), and the number of measurements and measurement data are stored in the nonvolatile memory 72. The microcomputer 70 calculates an average and a standard deviation of the measurement data, and judges that the measurements have completed normally if the standard deviation is within a given range (for instance, ±0.05 mm). If the standard deviation is out of this range, the microcomputer 70 judges that the measurement data include abnormal data due to, for instance, an error in eye fixation, and continues the measuring operation. A similar standard deviation judgment is performed while most deviated data is eliminated. An additional measurement is performed until a standard deviation comes within the given range.

If a measuring operation is interrupted (that is, the apparatus is rendered in a state that no cornea reflection images of a subject's eye are obtained) before the preset number of measurement data are obtained, the microcomputer 70 cancels the measurement mode after a lapse of a predetermined time.

If the preset number of measurement data have been obtained whose standard deviation is within the given range, the microcomputer 70 stops supplying power to the respective electrical circuits, thereby canceling the measurement mode. since an alignment mark and a mire ring image that have been observed through the observation window 10 disappear upon the cancellation of the measurement mode, the examiner can recognize that the measurement operation on one eye has been finished.

When the measuring unit 5 is moved together with the movable stage 3 to perform a measurement operation on the other eye, the micro switch 56 detects right/left switching and sends a detection signal to the microcomputer 70. In response, the microcomputer restarts supplying power to restore the apparatus to the measurement mode. As the examiner performs an alignment operation, the microcomputer 70 performs an operation similar to the above to produce measurement data for the other eye.

If at least the preset number of measurement data whose standard deviation is within the given range have been obtained for both eyes, the microcomputer 70 drives the printer 8 to print out the measurement data. Where some other data processing device, for instance, is connected to the apparatus, the microcomputer 70 transfers the measurement data to it. Although much deviated data are eliminated as described above, they may be included, if necessary, in the output data with a discrimination mark attached thereto.

After a lapse of a predetermined time (for instance, 3 minutes) from the data output, the microcomputer 70 stops supplying power to the peripheral circuits and turns off display, to thereby render the apparatus in an off state. When the movable stage 3 is thereafter moved due to, for instance, replacement of the subject, a signal is produced from the micro switch 56 and the apparatus again makes a transition to the measurement mode. When a measurement operation on a new eye is completed, previous data stored in the microcomputer 70 are subjected to rewriting.

After manipulating the power switch of the AC adaptor 9, the examiner is not required to manipulate any switches in a series of measurements from a start to data output. Printing and power-off of the main body of the measuring unit 5 may be effected as desired by using one of the switches 12.

What is claimed is:

1. An ophthalmologic apparatus comprising:
    measuring means for measuring an eye of a subject;
    a movable stage on which the measuring means is mounted;
    moving means for moving the movable stage horizontally relative to a fixed base stage;
    recognizing means for recognizing whether the measuring means has been moved by the moving means so as to go out of a predetermined range; and
    transition means for starting supply of power to the measuring means based on a recognition result of the recognizing means, to thereby render the measuring means operational.

2. The ophthalmologic apparatus according to claim 1, wherein the recognizing means comprises detecting means for detecting movement of the movable stage in a right-left direction.

3. The ophthalmologic apparatus according to claim 1, further comprising fixing means for prohibiting horizontal movement of the movable stage relative to the fixed base stage, the fixing means being provided in the movable stage and the fixed base stage and including a recessed member and a protrusive member to be fitted into the recessed member.

4. The ophthalmologic apparatus according to claim 1, further comprising:
    an alignment detection optical system for projecting alignment targets to the eye and for detecting the projected alignment targets;
    judging means for judging an alignment state based on a detection result of the alignment detection optical system; and
    measurement instructing means for instructing, based on a judgment result of the judging means, the measuring means to start measuring the eye.

5. The ophthalmologic apparatus according to claim 4, wherein the measurement instructing means instructs the measuring means to continue measuring the eye until obtaining a predetermined number of measurement values that satisfy a given standard.

6. An ophthalmologic apparatus comprising:
    measuring means for measuring an eye of a subject;
    a movable stage on which the measuring means is mounted;
    moving means having an operation lever incapable of inclination, for moving the movable stage horizontally relative to a fixed base stage;
    recognizing means for recognizing whether the measuring means has been moved by the moving means so as to go out of a predetermined range;
    transition means for starting supply of power to the measuring means based on a recognition result of the recognizing means, to thereby render the measuring means operational;
    an alignment detection optical system for projecting alignment targets to the eye and for detecting the projected alignment targets;
    judging means for judging an alignment state based on a detection result of the alignment detection optical system; and
    measurement instructing means for instructing, based on a judgment result of the judging means, the measuring means to start measuring the eye.

7. An ophthalmologic apparatus comprising:
    measuring means for measuring an eye of a subject;
    a movable stage on which the measuring means is mounted;

moving means for moving the movable stage horizontally relative to a fixed base stage;

first recognizing means for recognizing whether the measuring means has been moved by the moving means so as to go out of a predetermined range;

transition means for starting supply of power to the measuring means based on a recognition result of the first recognizing means, to thereby render the measuring means operational;

second recognizing means for recognizing whether the measuring means has completed output of measurement data;

stopping means for stopping the supply of the power to the measuring means based on a recognition result of the second recognizing means.

8. The ophthalmologic apparatus according to claim 7, further comprising:

third recognizing means for recognizing whether a predetermined measurement operation has been completed; and output instructing means for instructing the measuring means to output the measurement data based on a recognition result of the third recognizing means.

* * * * *